(12) United States Patent
Snyder et al.

(10) Patent No.: US 11,633,129 B2
(45) Date of Patent: Apr. 25, 2023

(54) NON-INVASIVE TRANSDERMAL SAMPLING AND ANALYSIS DEVICE INCORPORATING REDOX COFACTORS

(71) Applicant: Cambridge Medical Technologies LLC, Carson City, NV (US)

(72) Inventors: Helena Woodvine Snyder, Crozet, VA (US); Vikas Bhatia, Gaithersburg, MD (US); John Frederick Currie, Bethesda, MD (US); Emil F. Jachmann, New Canaan, CT (US)

(73) Assignee: Cambridge Medical Technologies LLC, Carson City, NV (US)

( * ) Notice: Subject to any disclaimer, the term of this patent is extended or adjusted under 35 U.S.C. 154(b) by 449 days.

(21) Appl. No.: 16/838,237

(22) Filed: Apr. 2, 2020

(65) Prior Publication Data
US 2020/0375510 A1    Dec. 3, 2020

Related U.S. Application Data

(60) Provisional application No. 62/829,938, filed on Apr. 5, 2019.

(51) Int. Cl.
*A61B 5/1486*    (2006.01)
*A61B 5/145*    (2006.01)
(Continued)

(52) U.S. Cl.
CPC ........ *A61B 5/14514* (2013.01); *A61B 5/1486* (2013.01); *A61B 5/1491* (2013.01);
(Continued)

(58) Field of Classification Search
CPC ............ A61B 5/14514; A61B 5/14546; A61B 5/1486; A61B 5/1491; A61B 5/6832; A61B 2010/008
See application file for complete search history.

(56) References Cited

U.S. PATENT DOCUMENTS 4,197,853 A    4/1980 Parker
4,526,176 A    7/1985 Bremer et al.
(Continued)

FOREIGN PATENT DOCUMENTS

EP    1 003 033 A1    5/2000
KR    10-2006-0082852 A    7/2006
(Continued)

OTHER PUBLICATIONS

Liu, Wenfang, and Ping Wang. "Cofactor regeneration for sustainable enzymatic biosynthesis." Biotechnology advances 25.4 (2007): 369-384 (Year: 2007).*

(Continued)

*Primary Examiner* — Andrey Shostak
(74) *Attorney, Agent, or Firm* — The Marbury Law Group, PLLC

(57) ABSTRACT

Systems and methods are provided for determining levels of an analyte in a biological fluid sample. A transdermal sampling and analysis device may include a substrate, at least one disruptor mounted on the substrate, a reservoir configured to collect and contain a biological fluid sample; a sensing element comprising at least two sensing electrodes, and at least one layer of a cofactor covering the sensing element in which the cofactor catalyzes a reaction to determine levels of an analyte in the biological fluid sample. The at least one disruptor of the transdermal sampling and analysis device may generate a localized heat capable of altering permeability characteristics of a stratum corneum layer of skin of an organism. The surface of at least one of the sensing electrodes of the transdermal sampling and analysis device may be coated with a sensing layer in which an enzyme immobilized within a hydrogel.

19 Claims, 9 Drawing Sheets

(51) Int. Cl.
*A61B 5/00* (2006.01)
*A61B 5/1491* (2006.01)
*A61B 10/00* (2006.01)

(52) U.S. Cl.
CPC ........ *A61B 5/14546* (2013.01); *A61B 5/6832* (2013.01); *A61B 2010/008* (2013.01)

(56) References Cited

U.S. PATENT DOCUMENTS

| | | | |
|---|---|---|---|
| 4,775,361 | A | 10/1988 | Jacques et al. |
| 4,821,733 | A | 4/1989 | Peck |
| 4,909,256 | A | 3/1990 | Peck |
| 5,019,034 | A | 5/1991 | Weaver et al. |
| 5,123,902 | A | 6/1992 | Muller et al. |
| 5,149,629 | A | 9/1992 | Rishpon et al. |
| 5,176,881 | A | 1/1993 | Sepaniak et al. |
| 5,203,327 | A | 4/1993 | Schoendorfer et al. |
| 5,284,748 | A | 2/1994 | Mroczkowski et al. |
| 5,330,527 | A | 2/1994 | Mroczkowski et al. |
| 5,362,307 | A | 7/1994 | Montecalvo et al. |
| 5,366,454 | A | 11/1994 | Currie et al. |
| 5,380,272 | A | 1/1995 | Gross |
| 5,458,140 | A | 10/1995 | Eppstein et al. |
| 5,711,861 | A | 1/1998 | Ward et al. |
| 5,722,397 | A | 3/1998 | Eppstein |
| 5,730,714 | A | 3/1998 | Guy et al. |
| 5,885,211 | A | 3/1999 | Eppstein et al. |
| 5,983,131 | A | 11/1999 | Weaver et al. |
| 5,985,116 | A | 11/1999 | Ikeda et al. |
| 6,022,316 | A | 2/2000 | Eppstein et al. |
| 6,046,051 | A | 4/2000 | Jina |
| 6,056,738 | A | 5/2000 | Marchitto et al. |
| 6,124,597 | A | 9/2000 | Shehada et al. |
| 6,144,869 | A | 11/2000 | Berner et al. |
| 6,175,752 | B1 | 1/2001 | Say et al. |
| 6,233,471 | B1 | 5/2001 | Berner et al. |
| 6,270,651 | B1 | 8/2001 | Essalik et al. |
| 6,281,006 | B1 | 8/2001 | Heller et al. |
| 6,342,037 | B1 | 1/2002 | Roe et al. |
| 6,393,318 | B1 | 5/2002 | Conn et al. |
| 6,436,078 | B1 | 8/2002 | Svedman |
| 6,464,649 | B1 | 10/2002 | Ishikawa et al. |
| 6,572,542 | B1 | 6/2003 | Houben et al. |
| 6,597,946 | B2 | 7/2003 | Avrahami et al. |
| 6,730,200 | B1 | 5/2004 | Stewart et al. |
| 6,887,202 | B2 | 5/2005 | Currie et al. |
| 6,922,586 | B2 | 7/2005 | Davies |
| 7,001,495 | B2 | 2/2006 | Thomas |
| 7,223,364 | B1 | 5/2007 | Johnston et al. |
| 7,287,318 | B2 | 10/2007 | Bhullar et al. |
| 7,826,981 | B2 | 11/2010 | Goode, Jr. et al. |
| 8,173,380 | B2 | 5/2012 | Yang et al. |
| 8,333,874 | B2 | 12/2012 | Currie et al. |
| 8,364,228 | B2 | 1/2013 | Currie et al. |
| 9,877,673 | B2 | 1/2018 | Currie et al. |
| 9,968,284 | B2 | 5/2018 | Vidalis et al. |
| 10,376,146 | B2 | 8/2019 | Mujeeb-U-Rahman et al. |
| 2001/0052459 | A1 | 12/2001 | Essalik et al. |
| 2002/0051975 | A1 | 5/2002 | Li et al. |
| 2002/0055704 | A1 | 5/2002 | Scott et al. |
| 2002/0086436 | A1 | 7/2002 | Buechler |
| 2002/0169394 | A1 | 11/2002 | Eppstein et al. |
| 2003/0003524 | A1 | 1/2003 | Taniike et al. |
| 2003/0100040 | A1 | 5/2003 | Bonnecaze et al. |
| 2003/0100846 | A1 | 5/2003 | Custer et al. |
| 2003/0130616 | A1 | 7/2003 | Steil et al. |
| 2003/0208152 | A1 | 11/2003 | Avrahami et al. |
| 2003/0214304 | A1 | 11/2003 | Karinka et al. |
| 2003/0225362 | A1 | 12/2003 | Currie et al. |
| 2004/0039343 | A1 | 2/2004 | Eppstein et al. |
| 2004/0058172 | A1 | 3/2004 | Summers et al. |
| 2004/0157319 | A1 | 8/2004 | Keen |
| 2004/0180391 | A1 | 9/2004 | Gratzl et al. |
| 2004/0193219 | A1 | 9/2004 | Asano et al. |
| 2004/0217018 | A1 | 11/2004 | Leong et al. |
| 2004/0224369 | A1 | 11/2004 | Cai et al. |
| 2004/0253304 | A1 | 12/2004 | Gross et al. |
| 2005/0042766 | A1 | 2/2005 | Ohman et al. |
| 2005/0045476 | A1 | 3/2005 | Neel et al. |
| 2005/0069454 | A1 | 3/2005 | Bell |
| 2005/0175505 | A1 | 8/2005 | Cantor et al. |
| 2005/0182307 | A1 | 8/2005 | Currie et al. |
| 2005/0226921 | A1 | 10/2005 | Kortzebom |
| 2005/0228340 | A1 | 10/2005 | Cleary et al. |
| 2006/0241514 | A1 | 10/2006 | Davies |
| 2006/0285996 | A1 | 12/2006 | Ohman et al. |
| 2009/0099434 | A1 | 4/2009 | Liu et al. |
| 2009/0281404 | A1 | 11/2009 | Currie et al. |
| 2009/0308742 | A1 | 12/2009 | Paranjape |
| 2010/0160755 | A1 | 6/2010 | Oviatt et al. |
| 2012/0073986 | A1 | 3/2012 | Jackson et al. |
| 2012/0150004 | A1 | 6/2012 | Currie et al. |
| 2012/0181189 | A1 | 7/2012 | Merchant |
| 2012/0187000 | A1 | 7/2012 | Kahn et al. |
| 2012/0245445 | A1 | 9/2012 | Black et al. |
| 2012/0283539 | A1 | 11/2012 | Freeman et al. |
| 2013/0131478 | A1* | 5/2013 | Simpson ............ A61B 5/14532 600/347 |
| 2013/0144142 | A1* | 6/2013 | Vidalis ............... A61B 5/14514 600/347 |
| 2014/0135679 | A1 | 5/2014 | Mann et al. |
| 2014/0275895 | A1 | 9/2014 | Vidalis et al. |
| 2015/0065818 | A1 | 3/2015 | Say et al. |
| 2015/0140584 | A1 | 5/2015 | Wilsey |
| 2016/0135721 | A1 | 5/2016 | Bollmann et al. |
| 2017/0325724 | A1 | 11/2017 | Wang et al. |
| 2018/0128766 | A1 | 5/2018 | Cardosi et al. |
| 2018/0338713 | A1 | 11/2018 | Polsky et al. |
| 2019/0076075 | A1 | 3/2019 | Miller et al. |
| 2019/0216374 | A1 | 7/2019 | Hoss et al. |

FOREIGN PATENT DOCUMENTS

| | | |
|---|---|---|
| WO | 97/19344 A1 | 5/1997 |
| WO | 99/56613 A1 | 11/1999 |
| WO | 2006/063063 A2 | 6/2006 |
| WO | 2007/070093 A2 | 6/2007 |
| WO | 97/42882 A1 | 11/2007 |
| WO | 2009/042631 A2 | 4/2009 |
| WO | 2011/053715 A2 | 5/2011 |
| WO | 2014/149514 A1 | 9/2014 |
| WO | 2018/237259 A1 | 12/2018 |
| WO | WO-2018237259 A1 * | 12/2018 ......... A61B 5/14532 |

OTHER PUBLICATIONS

International Search Report with Written Opinion cited in related Patent Application No. PCT/US2011/06558, 15 pages dated Jul. 25, 2012, (Jul. 27, 2012).

International Search Report and Written Opinion cited in related Patent Application No. PCT/US05/44287, 5 pages, (dated Aug. 28, 2006).

International Preliminary Examination Report cited in related Patent Application No. PCT/US01/17081, 5 pages, (dated Sep. 17, 2004).

Balabanova, et al., "Detection of Drugs in Sweat (Nachweis von Drogen im schweib)" Beitr. Gerichtl. Med., vol. 48, pp. 45-49, (1990).

Henderson et al., "Excretion of Methadone and Metabolites in Human Sweat," Research Communications in Chemical Pathology and pharmacology, vol. 5, No. 1, pp. 1-8, (Jan. 1973).

Peck et al., "Outward Transcutaneous Chemical Migration: Impliations for Diagnostics and Dosimetry", Skin Pharmacol, vol. 1, No. I, pp. 14-23, (1988).

Phillips et al., "A Sweat-Patch Test for Alcohol Consumption: Evaluation in Continuous and Episodic Drinkers", Alcohol: clinical and Experimental research, vol. 4, No. 4, pp. 391-395,(1980).

"SpectRx An Innovactive Medical Technology Company" [online], Copyright 2004, 1 p., Retrieved from the Internet: hhtp://www.spectrx.com. (Aug. 31, 2004).

(56) References Cited

OTHER PUBLICATIONS

Schneider et al., "B-Fit System: Bio-Flips Integrable Transdermal MicroSystem", ARO Workshop on Biomolecular Signaling, Energy Transfer, and Transduction Processes, Cashiers, NC, 16 pages, (May 14-17, 2000).
Smith et al., "Cocaine in Hair, Saliva, Skin Swabs, and Urine of Cocaine Users' Children", Forensic Science International, vol. 83, pp. 179-189, (1996).
International Preliminary Report on Patentability received in related Patent Application No. PCT/US2012/067265 dated Jun. 12, 2014.
Nijdam, A.J., et al., "Fluidic encapsulation in SU-8 [micro]-reservoirs with [micro]-fluidic through-chip channels", Sensors and Actuators A, vol. 120, p. 172-183; (Apr. 29, 2005).
Gadre et al., "Fabrication of a fluid encapsulated dermal patch using multilayered SU-8," Sensors and Actuators A: Physical, 114(2-3):478-485 (2004).
Paranjape et al., "A PDMS dermal patch for non-intrusive transdermal glucose sensing," Sensors and Actuators A: Physical, 104(3):195-204 (2003).
European Search Report dated Apr. 29, 2009, issued in US Application No. PCT/US2006023194, (May 13, 2009).
Xu, "Electrochemical Detection Optimized for Capillary Liquid Chromatographic Determination of Neuroactive Compounds", University of Pittsburgh, 137 pages, (Nov. 10, 2011).
Boder, et al., "Development of Monoclonal Antibodies for an Assay of Cardiac Tropinin-I and Preliminary Results in Suspected Cases of Myocardial Infarction", Clin. Chem. 38/11, pp. 2203-2214, (1992).
De Almeida, et al., "Measurement of Melatonin in body fluids: Standards, protocols and procedures", Childs Nerv. System 27, DOI 10.1007/s00381-010-1278-8, pp. 879-891, (2011).
Linder, et al., "Heparin-Binding Protein: An Early Marker of Circulatory Failure in Sepsis", Department of Clinical Sciences, Division of Infection Medicine, Lund University, Lund, Sweden, CID 2009:49, 8 pages, (Oct. 1, 2009).
Matsuyama, et al., "Soluble interleukin-6 receptors in inflammatory bowel disease: relation to circulating interleukin-6", GUT 36, pp. 45-49; (1995).
Wei, et al., "A novel sandwich immunosensing method for measuring cardiac troponin 1 in sera", Analytical Biochemistry 321, pp. 209-216, (2003).
Yanez, et al., "Development and Validation of an Ultrasensitive Procalcitonin Sandwich Immunoassay", MDPI, High-Throughput, 6, 18; doi:10.3390/ht6040018, www.mdpi.com/journal/hightroughtput, 12 pages, (2017).
Heller, et al., Electrochemical Glucose Sensors and their Applications in Diabetes Management, Chem Review, Department of Chemical Engineering, Univ. of Texas, (Sep. 17, 2007).
Merchant, et al., High-Sensitivity Amperometric Biosensors Based on Ferrocene-Modified Linear Poly (ethylenimine), Langmuir Article, 2009 American Chemical Society, (Mar. 24, 2009).
Merchant, et al., "Effect of Mediator Spacing on Electrochemical and Enzymatic Response of Ferrocene Redox Polymers", J. Phys. Chem. 114, pp. 11627-11634, (2010).
Xu, et al., Construction of phospholipid anti-biofouling multilayer on biomedical PET surfaces, Applied Surface Science 255, pp. 538-540, (2008).
Carneiro-Da-Cunha, et al., Physical and thermal properties of a chitosan/alginate nanolayered PET film, Carbohydrate Polymers 82, pp. 153-159, (2010).
International Search Report and Written Opinion cited in related Patent Application No. PCT/US2012/067265 dated Mar. 28, 2013.
International Preliminary Report on Patentability received in related Patent Application No. PCT/US2011/063558 dated Jun. 20, 2013.
International Search Report and Written Opinion issued for International Application No. PCT/US2014/027362, dated Sep. 1, 2014.
Xu, "Electrochemical detection optimized for capillary liquid chromatographic determination of neuroactive compounds", 2012, Doctoral Dissertation, University of Pittsburgh, Web, Retrieved from http://d-scholarship.pitt.edu/10478, 137 pages.
Huang, et al. "Catalytic and Inhibitory Kinetic Behavior of Horseradish Peroxidase on the Electrode Surface", Sensors, 12, 14556-14569 (2012).
International Search Report and the Written Opinion from the International Searching Authority in related Application No. PCT/US2020/065384 dated Apr. 19, 2021.
Currie, et al., "Novel Non-Intrusive Trans-Dermal Remote Wireless Micro-Fluidic Monitoring System Applied to Continuous Glucose and Lactate Assays for Casualty Care and Combat Readiness Assessment", Nato Otan, RTO HFM Symposium, RTO-MP-HFM-109, 18 pages, (Aug. 2004).
International Preliminary Report on Patentability from the International Bureau of WIPO cited in related Application No. PCT/US2020/065384 dated Sep. 9, 2022.

* cited by examiner

NON-INVASIVE TRANSDERMAL SAMPLING AND ANALYSIS DEVICE INCORPORATING REDOX COFACTORS

RELATED APPLICATIONS

This application claims priority to U.S. Provisional Patent Application No. 62/829,938 entitled "Non-Invasive Transdermal Sampling and Analysis Device Incorporating Redox Cofactors" filed on Apr. 5, 2019, the entire contents of which are hereby incorporated by reference for all purposes.

BACKGROUND

A biosensor is a device that may measure the presence or level of an analyte in a biological sample. A biosensor may include three main parts: i) biologically reactive elements sometimes referred to as reagents. Reagents may include biological materials (e.g., tissues, microorganisms, organelles, cell receptors, enzyme, antibodies, and take acid, etc.), a biologically derived material or biomimic, wherein the reagent may be created by biological engineering; ii) a transducer or detector element which may work in a physiochemical way (e.g., optical, piezoelectric, electrochemical, etc.) to transform the signal resulting from the interaction of the analyte being measured with the reagent into another signal that may be more easily measured and quantified; and iii) associated electronics and/or signal processors that may be primarily responsible for the display of the results.

Enzymatic amperometric biosensors involve placement of an enzyme in close proximity to an electrode surface. The enzyme involved may catalyze the reaction, which involves consuming of electroactive reactant or generation of electroactive species. The depletion or production process may then be monitored and may provide a direct measurement of the analyte concentration. Some enzymes that have attracted attention for detecting certain analytes work in the presence of a cofactor, which may bind to the active site of the enzyme and function as an intermediate carrier of electrons, specific atoms or functional groups.

SUMMARY OF THE INVENTION

Embodiment transdermal sampling and analysis devices may include a substrate, at least one disruptor mounted on the substrate, a reservoir configured to collect and contain a biological fluid sample, a sensing element comprising at least two sensing electrodes, and at least one layer of a cofactor covering the sensing element. In some embodiment transdermal sampling and analysis devices, the at least one disruptor may be configured to generate a localized heat capable of altering permeability characteristics of a stratum corneum layer of skin of an organism. In some embodiment transdermal sampling and analysis devices, the surface of at least one of the sensing electrodes may be coated with a sensing layer comprising an enzyme immobilized within a hydrogel. In some embodiment transdermal sampling and analysis devices, the cofactor may catalyze a reaction to determine levels of an analyte in the biological fluid sample.

In some embodiment transdermal sampling and analysis devices, the biological fluid sample may include interstitial fluid (ISF), and the enzyme may be an oxidoreductase. In some embodiment transdermal sampling and analysis devices, the cofactor may be oxidized nicotinamide adenine dinucleotide ($NAD^+$). In some embodiment transdermal sampling and analysis devices, the oxidoreductase may be selected from alcohol dehydrogenases or lactate dehydrogenases.

In some embodiment transdermal sampling and analysis devices, the hydrogel of the sensing layer may include a plurality of cross-linked hydrophilic polymer chains. In some embodiment transdermal sampling and analysis devices, the cross-linked hydrophilic polymer chains may include a linear poly(ethylenimine) (LPEI) coupled to an electron mediator. In some embodiment transdermal sampling and analysis devices, the electron mediator may be selected from the group consisting of a ferrocene, osmium bipyridine complexes, ruthenium phthalocyanine complexes, a quinone, a tetrathialfulvalene (TTF), a tetracyanoquinodimethane (TCNQ), or a thionine. In some embodiment transdermal sampling and analysis devices, the cofactor layer may be covered with at least one barrier layer that includes alginate. In some embodiment transdermal sampling and analysis devices, the at least one layer of the cofactor may include alginate.

Embodiment methods of determining levels of an analyte in a biological fluid sample may include creating a sensing element that includes a sensing layer and a sensing electrode, applying at least one layer of a cofactor atop the sensing layer, and providing the biological fluid sample to the sensing element and the at least one cofactor layer. In some embodiment methods, the sensing layer may include an enzyme immobilized in a polymer matrix, and the polymer matrix may be anchored to the sensing electrode. In some embodiment methods, the cofactor may not be bound to the sensing element. In some embodiment methods, molecules of the cofactor layer may freely dissociate into the biological sample.

BRIEF DESCRIPTION OF THE DRAWINGS

The accompanying drawings, which are incorporated herein and constitute part of this specification, illustrate exemplary aspects of the invention, and together with the general description given above and the detailed description given below, serve to explain the features of the invention.

DETAILED DESCRIPTION

Figure 1A:
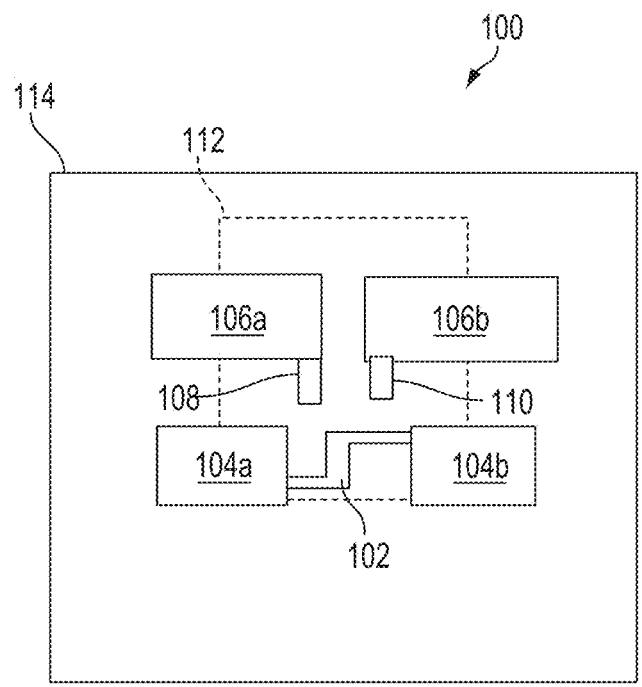
FIG. 1A is a component block diagram of a transdermal sampling and analysis device suitable for use with various disclosed embodiments.

The various embodiments will be described in detail with reference to the accompanying drawings. Wherever possible, the same reference numbers will be used throughout the drawings to refer to the same or like parts. References made to particular examples and implementations are for illustrative purposes, and are not intended to limit the scope of the disclosure or the claims. Alternate embodiments may be devised without departing from the scope of the disclosure. Additionally, well-known elements of the disclosure will not be described in detail or will be omitted so as not to obscure the relevant details of the disclosure.

The words "exemplary" and/or "example" are used herein to mean "serving as an example, instance, or illustration." Any embodiment described herein as "exemplary" and/or "example" is not necessarily to be construed as preferred or advantageous over other embodiments.

The term "in situ" is used herein to refer to tests and/or measurements performed using a natural composition/tissue in an environment that is at least partially subject to artificial control. For example, a novel transdermal biosensor may be said to be operating in situ when it is placed on the surface of a patient's skin while it disrupts the stratum corneum continuously to generate a biological fluid sample and analyze the generated biological fluid sample while the biosensor remains in place on the surface of the subject's skin.

Biosensors combine a biological sample with a physiochemical detector component (i.e., reagent) to allow for the detection of an analyte (that is, a substance or chemical constituent that is determined in an analytical procedure).

The signal, generated as a result of interaction between the detector and the analyte may be electrical, optical, thermal, etc., is transformed by the means of suitable transducer element into a measurable parameter such as current or voltage. The biosensor selectivity against the target analyte may be determined by the physiochemical detector, while sensitivity may be dependent on the transducer.

In a number of biosensor applications, it may be beneficial to detect small quantities of target analyte in small volumes. Therefore, there is a need to develop biosensors that exhibit high sensitivity and low detection limits High current output and sensor sensitivity in the case of enzymatic amperometric reactions may leverage the efficient transfer of electrons between the enzyme's redox center and a biosensor electrode surface. Depending on the system design, the availability of a cofactor or lack thereof may limit the overall reaction rate and consequently the signal output that ultimately quantifies presence of analyte in a sample.

Compared to other detection methods, such as colorimetric methods, chemiluminescence, fluorimetric methods, high performance liquid chromatography (HPLC), and magnetic resonance spectroscopy, amperometric biosensors have shown advantages such as simplicity, portability, rapid response, high specificity, and simple operation. In particular, amperometric biosensors may be convenient for monitoring small molecule concentrations. Amperometric biosensors may be based on an enzyme that has the ability to catalyze a reaction involving the analyte. Such reactions may involve the consumption an electroactive reactant and/or production of an electroactive product. The depletion of the electroactive reagent or production process of the electroactive product may be monitored amperometrically to provide a direct measurement of the analyte concentration. Specifically, electrons from the enzyme-catalyzed redox reaction may be transferred to an electrode (e.g., a working electrode), and the electric current flow resulting from the transfer of electrons may be used as a measure of the analyte. From the current flow level an analyte concentration in the original sample may be deduced. Amperometric biosensors measure the electric current generated between the working electrode and a counter electrode when the potential between them may be maintained at a constant level by means of a potentiostat. Such biosensors are typically based on enzymes that either consume oxygen, generate hydrogen peroxide, or indirectly produce a reduced form of a cofactor (e.g., NADH, NADPH, $FADH_2$, coenzymeQ, etc.) with the catalytic breakdown of a substrate Biosensors designed for patient (also referred to as a subject) home monitoring generally measure electric current produced by an enzyme-catalyzed redox reaction in an electrochemical cell involving an analyte of interest for medical purposes (e.g., glucose, etc.). The sample used for analysis may be a blood droplet collected from a subject's finger, arm, or other location on the body. In addition to being painful, these conventional biosensors are also designed in a manner so as to require a relatively large fluid sample to accurately determine analyte concentration. For example, the currently available conventional blood glucose biosensors require at least 300 nl of blood in order to analyze the blood glucose levels. To obtain these larger biological samples, painful and invasive procedures must be employed, which are not desirable.

Another disadvantage of the conventional biosensors is that they require several steps before they can analyze a biological sample. Conventional biosensors require loading a lancing device with a disposable tip, loading a test strip into an analyzer, breaching the skin, collecting the biological samples (e.g., blood), depositing the biological sample onto the test strip, and disposal of the sharp tip and blood-laden test strip. This multi-step process is time consuming and may cause contamination or loss of the biological sample during the collection and/or delivery.

The terms "transdermal sampling and analysis device" and "transdermal biosensor" are used interchangeably herein to refer to a one-step transdermal biosensor that provides in situ measurement of analyte concentrations from small quantities of the interstitial fluid collected from the capillary-like channels of a subject's skin. Examples of such transdermal sampling and analysis devices and methods for their manufacturer are described in: U.S. Pat. No. 9,877,673, entitled "Transdermal Sampling and Analysis Device," in U.S. patent application Ser. No. 14/208,344, entitled "Methods of Manufacture to Optimize Performance of Transdermal Sampling and Analysis Device," in International Published Application No. WO2007/070093, entitled "Flexible Apparatus and Method for Monitoring and Delivery," in U.S. Pat. No. 8,364,228, entitled "Apparatus and Method for Continuous Real-time Trace Biomolecular Sampling, Analysis, and Delivery," and in the publication entitled "Novel Non-Intrusive Trans-Dermal Remote Wireless Micro-Fluidic Monitoring System Applied to Continuous Glucose and Lactate Assays for Casualty and Combat Readiness Assessment" by John F. Currie, Michael M. Bodo and Frederick J. Pearce, RTO-MP-HFM-109:24-1, Aug. 16, 2004, the contents of which are hereby incorporated by reference for the purpose of describing the device and methods disclosed therein.

The transdermal biosensor may also enable the entire process of analyzing a biological sample including disrupting the skin cells, collecting biological samples, reacting the biological sample with a biologically reactive element, and sensing the signals generated by the reaction in singular device. In contrast, in in vitro measurements, such as those performed using conventional blood tests or withdrawal techniques, a biological sample (e.g., ISF) may be collected, and subsequently tested for an analyte (or other measurable property) by submitting it to a remote assay or sensor. By incorporating a transdermal sampling device and analyzing device in a singular in situ test, a smaller biological sample may be utilized and the potential for contamination of the biological sample may be dramatically reduced. Moreover, the time required to obtain a sample and perform an analysis of the sample may be also reduced.

In such transdermal analysis and sensing devices/biosensors, a subject's stratum corneum may be disrupted through the application of localized heat to allow interstitial fluid to permeate from capillary-like channels in the subject's skin for sampling, collection, and analysis. The sampled and collected fluids may be tested for an analyte by reacting the collected fluids to a biologically reactive element, such as an enzyme (e.g., an oxidoreductase). The products of a biochemical reaction between the collected fluid sample and the biologically reactive element may be analyzed electrochemically to compute the concentration of the analyte (also referred to as "reactant") from either an electric potential or an electrical current. The amount of electric potential or current that is detected may be mapped to determine the concentration levels of analytes or characteristics of the collected fluid sample. Once the disruptor unit of the transdermal analysis and sensing devices/biosensors is removed from the skin, stratum corneum cells become impermeable again by returning to their original formation and closing the capillary-like channels.

FIG. 1A is a block diagram illustrating the functional components of an example transdermal sampling and analysis device 100. A transdermal sampling and analysis device 100 may include a disruptor 102 connected to the positive and negative electrical poles of a signal generator 104a, 104b. In an embodiment, the disruptor 102 may function as a resistive element. The disruptor 102 produces heat as electrical current is applied through the disruptor 102. When placed on the skin, the localized heat generated by the disruptor 102 element may cause disruption to the skin cells facilitating the flow of interstitial fluid onto the surface of the transdermal sampling and analysis device 100. The disruptor 102 may be made from a variety of materials which exhibit the appropriate heating and control properties to provide the precise heating control properties required to disrupt the skin cells without damaging them. After a brief period of increased permeability due to the application of localized heat, the skin cells return to their normal function and may become impermeable again to retain their interstitial fluid.

The materials used to create the disruptor 102 may be selected for relative ease of manufacture as well as cost considerations. Materials such as titanium, tungsten, stainless steel, platinum and gold may be preferably used to form the disruptor 102. In a preferred embodiment, gold may be used to form the disruptor 102.

In an embodiment, when analyzing concentrations of an analyte in an obtained biological fluid sample (e.g., interstitial fluid), enzymatic reactions involving the analyte may yield electrons that may be captured to generate anodic current between a counter electrode 108 and a working electrode 110, also referred to as sensing electrodes 108, 110. Such reactions may include, for example, the conversion of ethanol to acetaldehyde, of lactate to pyruvate, of glucose to gluconolactone, or others. The magnitude of the electrical current generated across the working electrode 110 and the counter electrode 108 as a result of this enzyme-catalyzed reaction may be proportional to the amount or concentration of the analyte contained in the obtained biological fluid sample. In an embodiment, a voltage potential may be applied to at least the working electrode 110 using a power generator (not shown).

In such a scenario, the working electrode 110 may function as an anode and the counter electrode 108 may function as a cathode of an electrolytic cell, or vice versa. The magnitude of the current generated may be measured by an ammeter, the measurement of which may directly correlate to the amount (or concentration) of analyte in the collected biological fluid sample.

A transdermal sampling and analysis device 100 may further include a reservoir 112 for collecting and containing biological samples such as interstitial fluids that flow from capillary-like channels in disrupted stratum corneum. The reservoir 112 may be formed under the disruptor 102 and sensing electrodes 108, 110. When the transdermal sampling and analysis device 100 is place on the subject's skin with the disruptor 102 contacting the skin, the reservoir may effectively be positioned above the disruptor 102 and sensing electrodes 108, 110 to contain the released fluid sample. The reservoir 112 may include a cover or lid to more effectively contain the fluid sample. A reservoir 112 may be created using conventional methods known in the art, for example, by the buildup of material by additive process or by subtractive process such as photolithography. A substrate 114 may form the support upon which transdermal sampling and analysis device 100 components may be positioned or attached. Because the obtained biological fluid sample may be analyzed without removing the device from the subject, the process is referred to as an n situ process.

Figure 1B:
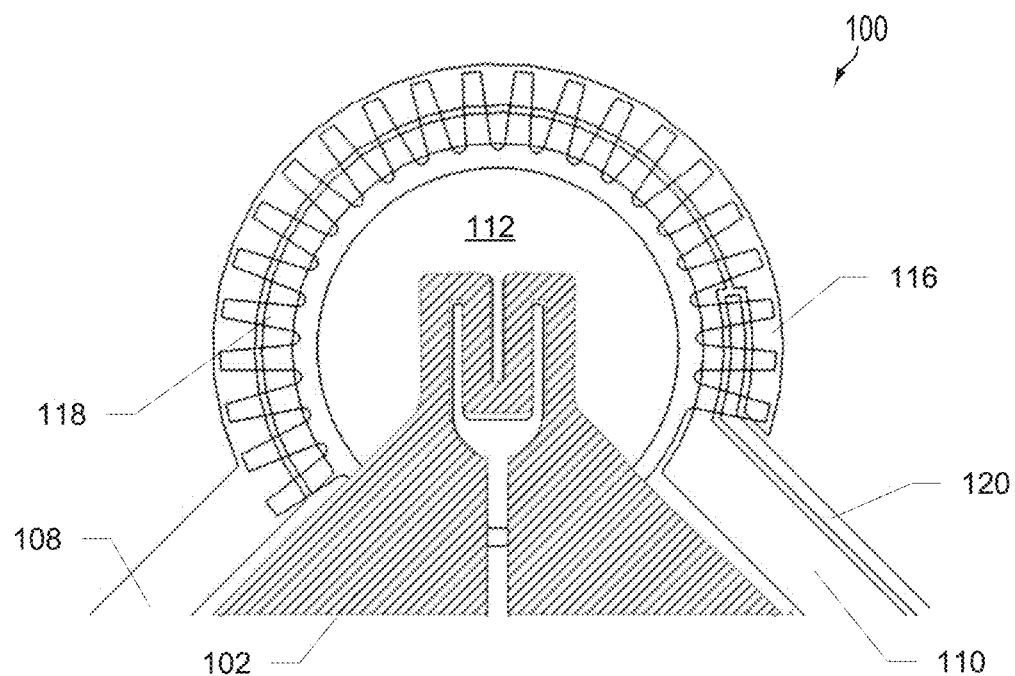
FIG. 1B is a top view of another transdermal sampling and analysis device suitable for use with various disclosed embodiments.

FIG. 1B illustrates an alternative embodiment of the transdermal sampling and analysis device 100. The transdermal sampling and analysis device 100 may include a disruptor 102 having a serpentine configuration, within a collection reservoir 112. Leads capable of coupling the disruptor 102 to a voltage/current source may be extended to the corners of the transdermal sampling and analysis device 100. The disruptor 102 may be also positioned within a hole in a lid layer so that the disruptor 102 may be exposed to and may directly contact the subject's skin for disruption of the stratum corneum and the production of a biological fluid sample. A sensing chamber 116 may form a circular shape around the periphery of the collection reservoir 112. The sensing chamber 116 may contain sensing channels 118 in a radial arrangement. The circular sensing channels 118 may guide the flow of a biological fluid sample through the circular-shaped sensing chamber 116. The sensing chamber 116 may provide the biological fluid sample over the entire surface of the counter electrode 108 and the working electrode 110. A reference electrode 120 may optionally be included. The disruptor 102, counter and working electrodes 108, 110, and optional reference electrode 120 may be all formed on a substrate layer.

Many different analysis techniques may be incorporated into the transdermal sampling and analysis unit 100 to determine the levels and concentrations of various analytes in a biological fluid sample. For example, amperometric, coulometric, potentiometric techniques may be each alternative techniques that may be incorporated into the transdermal sampling and analysis device 100 to determine levels or concentrations of analytes in a biological fluid sample. In addition, electrochemical impedance analysis techniques may be incorporated to detect the presence of particular antibodies in a biological fluid sample.

The counter and working electrodes 108, 110 may be made from any of a variety of materials which exhibit satisfactory conductivity characteristics and appropriate to the specific measurement used. In addition, the materials used to create the electrodes 108, 110, 120 may be selected for relative ease of manufacture as well as cost considerations. Examples of materials exhibiting satisfactory conductivity characteristics for use as the counter electrode 108 and the working electrode 110 may include gold, platinum, silver, carbon or other materials.

Selection of a substrate 114 for the transdermal sampling and analysis device 100 may depend on the coefficient of thermal expansion and conductivity of the material used to make the disruptor 102 of the transdermal sampling and analysis device 100. For example, the substrate 114 may be made of a material which has a coefficient of thermal expansion (CTE) that deviates from the CTE of the material used in the disruptor 102 by less than 50%, and preferably by less than 10%. In a further embodiment, the substrate 114 may be made of a material which has a coefficient of thermal conductivity (CTC) that is lower than 0.5 W/(m·K).

A sensing layer including an enzyme may be applied to the surface of at least one of the sensing electrodes 108, 110, such as the working electrode 110. By applying a voltage (or current) across the terminals of the disruptor 102, a precision controlled heat may be produced and localized to the disruptor site. The localized heat may be applied against the subject's skin to alter the permeability of the skin cells and consequently creates capillary-like channels. As the stratum corneum is disrupted, biological interstitial fluid may begin to flow through the stratum corneum into the reservoir 112 by capillary action of the structure. Interstitial fluid may flow out of the capillary-like channels into the reservoir 112 and over the surface of the counter electrode 108 and the working electrode 110. The obtained biological fluid sample (i.e., interstitial fluid) may come into contact with the sensing layer coating the surface of the working electrode 110, causing a chemical reaction that releases energy in the form of electrons. The electrons released due to the reaction may travel through the working electrode 110 towards the counter electrode 108, generating a current.

The transdermal sampling and analysis device 100 may be designed to deliver heat to the subject's skin with a power density of 1-10 W per $mm^2$. In a preferred embodiment the disruptor 102 delivers heat to the subject's skin with a power density of 2-5 W per $mm^2$. The transdermal sampling and analysis devices 100 may be made using a variety of different disruptor 102 configurations. The size and shape of the disruptor 102 may affect the resistive characteristics of the disruptor 102 and consequently, the ability of the disruptor 102 to generate a localized heat. In addition, the material selected to form the disruptor 102 may affect the resistive characteristics of the disruptor 102 and consequently, the ability of the disruptor 102 to generate a localized heat. As with sensing electrode 108, 110 material selection, disruptor 102 materials may be selected from a wide variety of materials exhibiting satisfactory electrical conductance/resistive properties such that sufficient heat may be generated when specific voltages are applied to the disruptor 102 leads. In addition, thermal conduction and resistance characteristics should be observed in an optimal disruptor 102 material. Finally, ease of manufacturing processing and cost may determine the final selection of disruptor material. For example, a disruptor 102 may be made of nichrome, titanium, tungsten, or gold. In a preferred embodiment, the disruptor may be made from gold.

Figure 2:
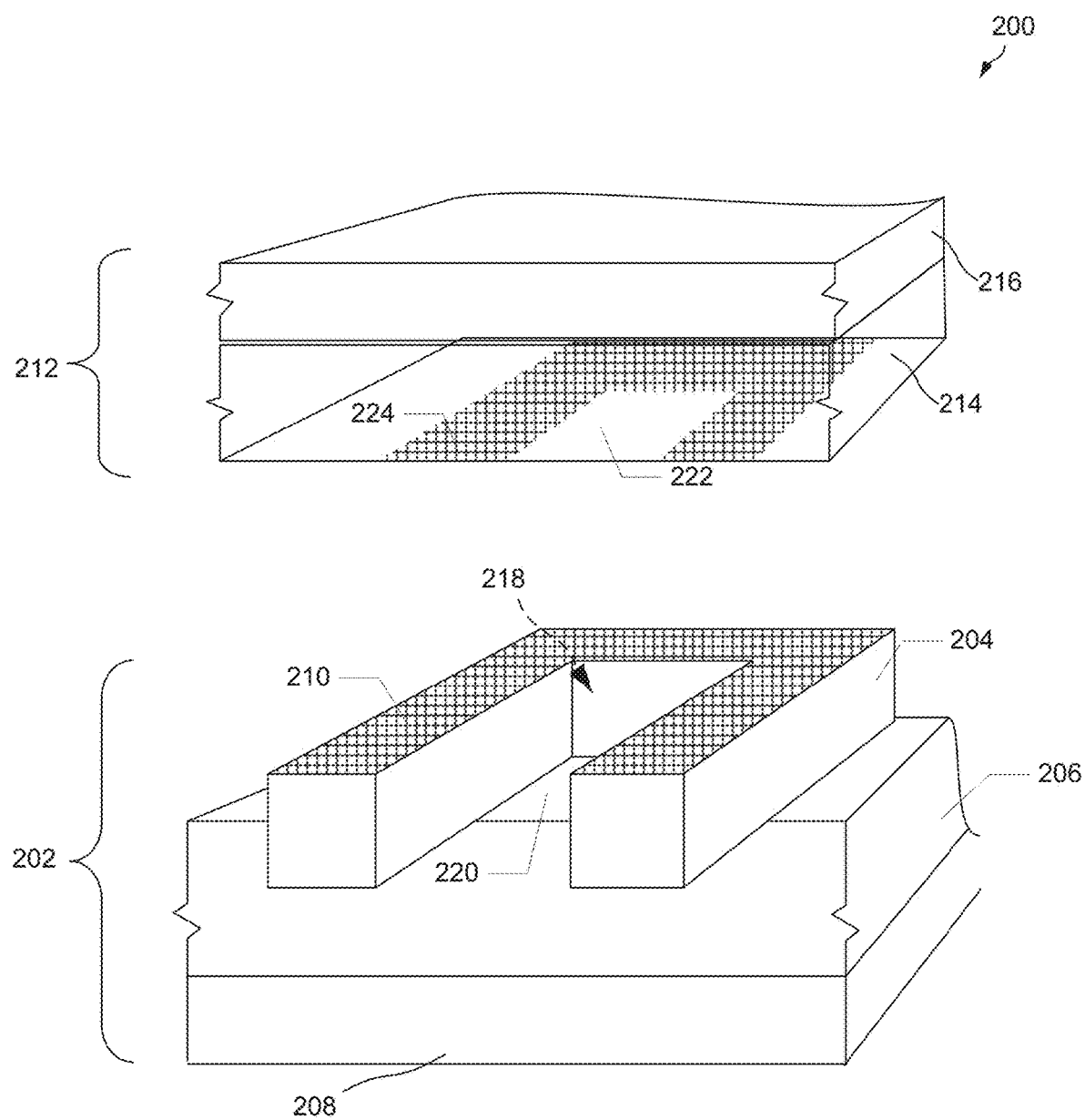
FIG. 2 is a perspective view of a portion of a lid and base structure of another transdermal sampling and analysis device suitable for use with various disclosed embodiments.

FIG. 2 illustrates a transdermal sampling and analysis device 200 according to an alternative embodiment. With reference to FIGS. 1A-2, the device 200 (not drawn to scale) may be formed using techniques similar to those discussed above with respect to transdermal sampling and analysis device 100. Representative components of the transdermal sampling and analysis device 200 may include a base structure 202 that includes a spacer layer of channel support structures 204 formed over a counter electrode 206, which are both formed over a base substrate 208. An adhesive (not shown) may be applied to the top surface 210 of the channel support structures 204. A lid structure 212 of the transdermal sampling and analysis device 200 may have a working electrode 214 patterned onto a lid substrate 216. A layer of analyte sensing reagent (not shown) may be applied to the surface of the working electrode 214. The base structure 202 and lid structure 212 illustrate representative cross-section segments of a larger, three dimensional device transdermal sampling and analysis device 200, and are not meant to limit the device 200 based on size or shape. Further, while the base structure 202 is shown with two spacer layer channel support structures 204, they are representative of any of a plurality of sets of channel support structures that may be formed across a larger base structure.

As the lid structure 212 is brought down into position over the channel support structures 204, the adhesive (not shown) on the channel support structures 204 may secure the lid structure 212 by contacting the working electrode 214. In this manner, channels 218 may be formed between exposed areas 220 of the counter electrode 206 and exposed areas 222 of the working electrode 214. Such exposed areas on both the working electrode 214 and the counter electrode 206 electrodes may be defined around the direct contact between the top surface 210 of the spacer layer channel support structures 204 and a corresponding contact area 224 on the surface of the working electrode 214.

In an alternative embodiment, an additional spacer layer may be applied atop the channel forming spacer layer (i.e., channel support structures). In the various embodiments, the second spacer layer may be recessed back from the channel support structures in order to provide lift space between the channel support structures and a substantial portion of the working electrode surface.

While not limited to particular dimensions, in some embodiments the second spacer layer may be approximately the same thickness as the channel forming spacer layer. In an embodiment, the total thickness of the channel forming spacer layer and second spacer layer may be approximately the same as that of the single channel forming spacer layer, such as that of channel support structures 204. In this manner, the depth of the sensing channels (i.e., vertical space between the counter and working electrodes) may remain the same to avoid requiring a greater amount of fluid to fill.

Figure 3:
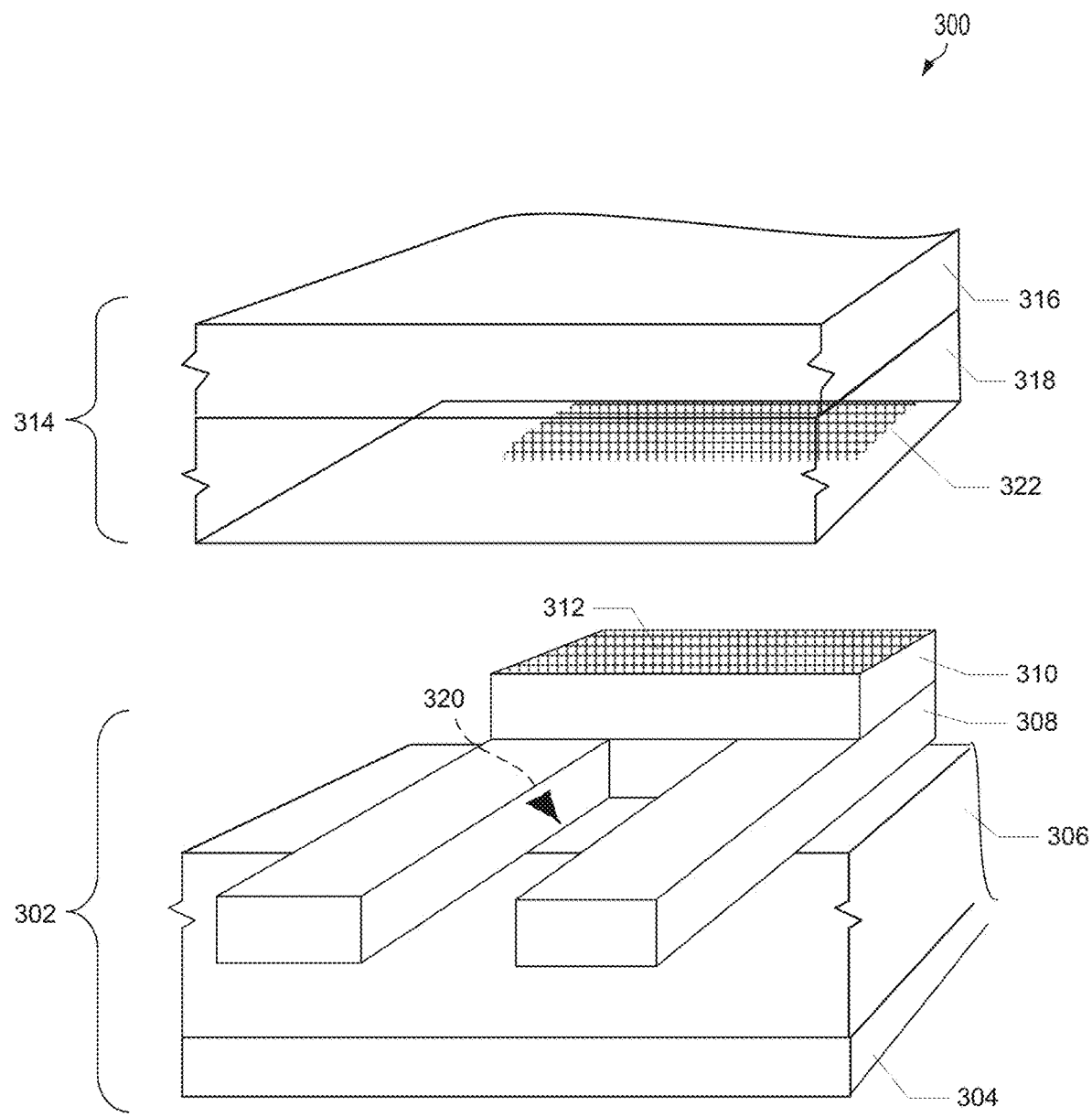
FIG. 3 is a perspective view of a portion of a lid and base structure of another transdermal sampling and analysis device suitable for use with the various disclosed embodiments.

FIG. 3 illustrates a transdermal sampling and analysis device 300 according to an alternative embodiment. With reference to FIGS. 1A-3, a base structure 302 may include a first conductive material layer applied to a base substrate 304, and patterned to form components including at least a counter electrode 306. Transdermal sampling and analysis device 300 may also have a photoresist material applied over the counter electrode 306, which may be patterned to form channel support structures 308 in a channel forming spacer layer.

A second spacer layer material may be applied over the channel forming spacer layer to form a recessed second spacer layer 310. The degree to which the second spacer layer 310 is recessed back from the edge of the channel support structures 308 may be variable according to different embodiments. Also depending on the type of material used to create the second spacer layer 310, an adhesive material may be selectively applied to the top surface 312 of the second spacer layer 310. For example, the second spacer layer 310 material may be a double sided adhesive, thereby making an additional adhesive layer unnecessary. In various embodiments, the second spacer layer 310 as well as the channel forming spacer layer may each be around 10-20 μm thick.

A lid structure 314 of the transdermal sampling and analysis device 300 may include a lid substrate 316 to which a second conductive material layer may be applied. The second conductive material layer may be patterned to form a working electrode 318, and a layer of the analyte sensing reagent (not shown) may be applied to the surface of the working electrode 318. As shown by the base structure 302 of device 300, channels 320 may be formed between exposed areas of the counter electrode 306 and exposed areas of the working electrode 318.

While the exposed areas on the counter electrode 306 may be defined by channel support structures 308, similar to device 200 in FIG. 2, such channel support structures 308 do not limit the exposed areas of the working electrode 318. Rather, the recessed second spacer layer 310 may serve to raise the working electrode 318 off of the channel support structures 308, thereby providing a larger exposed area on the working electrode 318. That is, the only direct contact to the working electrode 318 of transdermal sampling and analysis device 300 is by the top surface 312 of the recessed spacer layer 310. As a result, transdermal sampling and analysis device 300 may have a smaller corresponding contact area 322 on the working electrode 318 in comparison to the contact area 224 of transdermal sampling and analysis device 200. The larger exposed areas of the working electrode 318 may provide a stronger signal and/or allow for use of a smaller working electrode to produce the same level of result.

Since different subjects may have different skin thickness levels, calibration of the transdermal sampling and analysis device 100, 200, 300 may be required to generate sufficient heat to obtain the optimal amounts of biological fluid samples with the least amount of sensation. Thus, the level and duration of the temperature of the disruptor 102 may be adjusted for different subjects. Preferably, disruption of the skin may occur when heat of 140° C. from the disruptor 102 may be supplied to the skin surface for duration of about 140 ms. Further, one or more barrier elements may be employed in the transdermal sampling and analysis biosensor device 100, 200, 300 to prevent or reduce interference from other biological species in the interstitial fluid, which could negatively impact the accuracy of the results.

Amperometric biosensors utilize the electrical current produced when an oxidation or reduction reaction occurs at an electrode, such as one of the sensing electrodes 108, 110 (e.g., working electrode 110, 214, 318); measurement of electrical current generated during the reaction is directly proportional to concentration of that species present in the particular sample. Thus, amperometric biosensors function by measuring the electrical current produced through the application of an electrical potential across working and reference electrodes that results from the electrocatalytic oxidation or reduction of the involved electroactive species. The magnitude of the measured electrical current is directly correlated to the concentration of a redox-active reagent or product in an enzymatic reaction. Generally, a biosensor for detection of L-lactate in tissue or blood focuses on enzymatic amperometric sensors owing to their simple design and performance.

The enzyme utilized in such biosensors may have the ability to catalyze a reaction involving the analyte with the consumption of an electroactive reactant and/or the production of an electroactive product. The depletion or production process is then monitored amperometrically and gives a direct measurement of the analyte concentration.

In general, the concept behind such a biosensor is the fact that an immobilized enzyme catalyzes the oxidation of a substrate. In order to work as a catalyst, certain enzymes require the presence of a redox cofactor. For example, an oxidized form of the redox cofactor (e.g., nicotinamide adenine dinucleotide ($NAD^+$), flavin adenine dinucleotide (FAD), etc.) may be the initial electron acceptor, and converted into a reduced form (e.g., NADH, $FADH_2$, etc.) during the reaction. In a typical reaction cycle using such an enzyme, a substrate ($X-H_2$) may bind to the enzyme active site and interact with the cofactor to generate an oxidized product (X) a, the reduced cofactor, and, in some reactions, $H^+$. This is shown in Eq. 1 below:

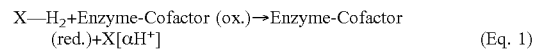

$$X-H_2 + \text{Enzyme-Cofactor (ox.)} \rightarrow \text{Enzyme-Cofactor (red.)} + X[\alpha H^+] \quad (\text{Eq. 1})$$

Some biosensors measure the amount of the reduced form of the cofactor that is generated during this reaction. In particular, $NAD^+$ is an important cofactor since $NAD^+$ participates in enzymatic catalysis of a large number of oxidoreductases, including more than 300 dehydrogenase enzymes. NAD-dependent oxidoreductases are widely used in bioprocesses and analytical applications. Therefore, there is an increasing interest in the electrochemistry of the $NAD^+$/NADH redox couple for electrodes in various biosensing devices. Examples of enzymes that require $NAD^+$ include, but are not limited to, alcohol dehydrogenase (ADH), lactate dehydrogenase (LDH), glyceraldehyde phosphate dehydrogenase, pyruvate dehydrogenase, α-keto-glutarate dehydrogenase, isocitrate dehydrogenase, malate dehydrogenase, hydroxy-acyl-SCoA dehydrogenase, etc.

For example, an alcohol detection sensor may be provided that is more reliable and accurate than breathalyzer applications. Biosensors based on alcohol dehydrogenase (ADH) may be of particular interest for ethanol analysis due to the toxicological and psychological effects of ethanol in the human body. ADH, which is selective for primary aliphatic and aromatic alcohols, catalyzes the conversion of ethanol to acetaldehyde by reduction of $NAD^+$. In this reaction, two hydrogen atoms and two electrons are removed from the ethanol molecule. One of the hydrogen atoms and both electrons are subsequently transferred to $NAD^+$, generating NADH and $H^+$.

As another example, lactate dehydrogenase (LDH) is an enzyme that may be of important medical significance for use in biosensors for lactate analysis. Specifically, an elevated lactate level may be an indication of lack of oxygen (hypoxia) or the presence of other conditions that cause excess production or insufficient clearing of lactate from the system. LDH has a high catalytic activity for conversion of lactate to pyruvate in the presence of a cofactor (NAD or NADP). In particular, in the presence of $NAD^+$, two hydrogen atoms and two electrons are removed from the lactate molecule. One of the hydrogen atoms and both electrons are transferred to $NAD^+$, generating NADH and $H^+$.

In a biosensor, for each of these example dehydrogenase reactions, NADH may transport electrons between the enzyme and a sensing electrode (e.g., working electrode 110, 214, 308). At the sensing electrode surface, NADH is oxidized under the influence of an applied potential, regenerating $NAD^+$ and producing a current that is directly proportional to the concentration of analyte in the sample (e.g., ethanol or lactate).

The direct oxidation of NADH to regenerate $NAD^+$ at the sensing electrode takes place at considerable overpotentials. To enable oxidation at lower potentials, an electron mediator may be immobilized on the surface of the sensing electrode, such as within a polymer matrix. In some embodiments, the polymer matrix may be formed from mediator-coupled polymer chains (e.g., Fc-LPEI). The polymer matrix may be a hydrogel—that is, a polymeric network of interconnected hydrophilic polymer chains—created by cross-linking the enzyme with the mediator-coupled polymer chains. In this manner, the enzyme may be immobilized.

Other polymers that may be used to create a matrix that immobilizes the mediator and/or enzyme in the sensing layer include, but are not limited to, the following polyions: poly(styrene)-co-styrene sodium sulfonate (NaPSS); polyvinylsilane (PVS); poly{1-4[4-(3-carboxy-4-hydroxyphenylazo) benzenesulfonamido]-1,2-ethanediyl sodium salt}; (PAZO); poly (1-acrylamido-1-methyl-1-propane sulfonic acid) (PAPSA); Poly[bis(4-phenyl)(2,4,6-trimethylphenyl) amine] (PTAA); poly(2-acrylamido-2-methyl-1-propanesulfonic acid) (PAMPSA); polystylenemethylenediethylmethylamine (PSMDEMA); poly(allylamine hydrochloride) (PAH); precursors to poly(p-phenylenevinylene) (Pre-PPVs); poly (diallyldimethylammonium chloride) (PDDA); polyetherimide (PEI); poly(p-pyridyl vinylene) (PHPyV); and sulfonated polyaniline (SPAn).

In such systems, the mediator may be reduced by the enzyme, with the reduced form of the mediator in turn being reoxidized at the surface of the sensing electrode surface to provide the amperometric signal. Examples of mediators that may be used in the biosensors of various embodiments may include transition metal compounds, conducting polymers, and organic dyes. Transition metal compound-based mediators may include complexes with ferrocene (i.e., "Fc") ($Fe(C_5H_5)_2$), ferrocenecarboxaldehyde ($C_{11}H_{10}FeO$), ferricyanide ($Fe(CN)_6^{3-}$), Prussian blue, cobalt phthalocyanine, ruthenium phthalocyanine, osmium complexes with a variety of redox polymers (e.g., osmium bipyridyl complex ($C_{20}H_{16}C_{12}N_4Os$)), or other transition metal compounds. Conducting polymer-based mediators may include poly(aniline)-poly(acrylate), poly(aniline)-poly(vinylsulfonate), poly(pyrrole), poly(pyrrole)-poly(vinylsulfonate), poly(vinylpyrrolidone), or other polymers. Organic dye-based mediators may include methylene green, Meldola blue, tetrathiafulvalene, thionine, tetracyanoquinodimethane (TCNQ), or quinine groups.

Figure 4A:
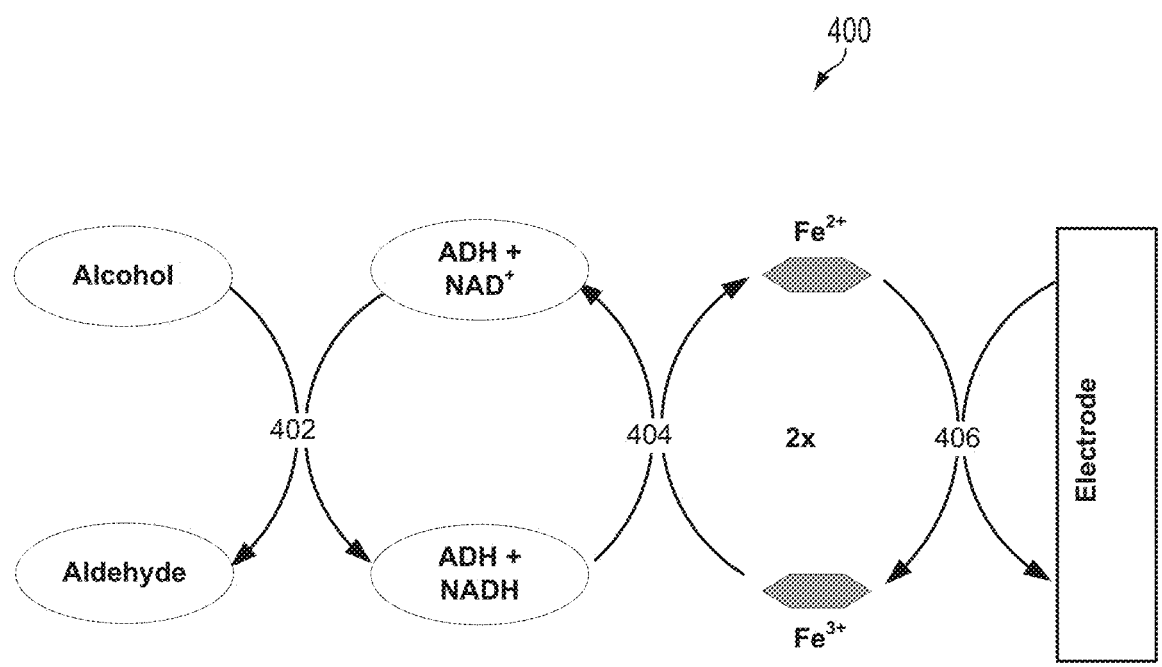
FIG. 4A is a schematic illustration of an example reaction in an alcohol biosensor.
Figure 4B:
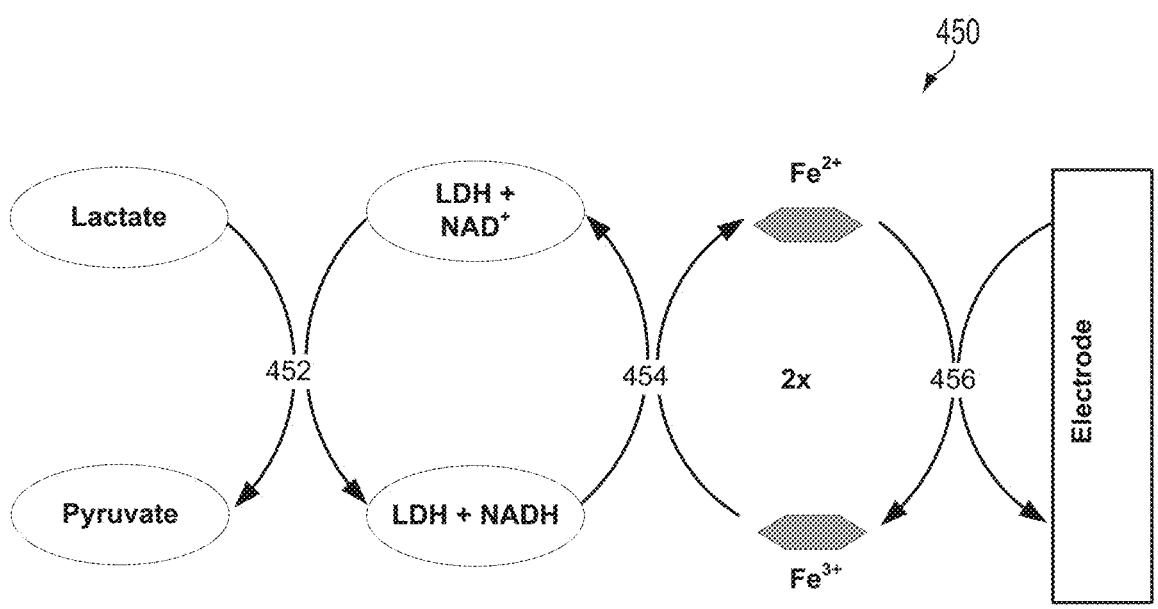
FIG. 4B is a schematic illustration of an example reaction in a lactate biosensor.

The example reactions shown in FIGS. 4A and 4B illustrate the general steps that may occur to measure analyte concentrations in transdermal biosensors that use ADH or LDH. With reference to FIGS. 1A-4B, the transdermal biosensors that use ADH or LDH may be similar to the transdermal sampling and analysis devices 100, 200, 300.

In reaction 400 ADH in the presence of $NAD^+$ may catalyze a breakdown of an alcohol (e.g., ethanol) present in interstitial fluid to an aldehyde (e.g., acetaldehyde), step 402. In step 404, the resulting NADH may be reoxidized by reducing the oxidized form of a mediator (i.e., ferrocenium), converting it to its reduced form (i.e., ferrocene). The mediator in turn may be reoxidized by reducing a sensing electrode (e.g., working electrode 110, 214, 318), step 406, to generate an electrical current.

In similar reaction 450, LDH in the presence of $NAD^+$ may catalyze a breakdown of lactate in the interstitial fluid to pyruvate, step 452. In step 454, the resulting NADH may be reoxidized by reducing the oxidized form of a mediator (i.e., ferrocenium), converting it to its reduced form (i.e., ferrocene). The mediator in turn may be reoxidized by reducing the sensing electrode (e.g., working electrode 110, 214, 318), step 456, to generate an electrical current in the same manner as in FIG. 4A.

Therefore, in both reactions 400 and 450, the electron mediator may transfer electrons to a sensing electrode (e.g., 110, 214, 318), where anodic potential has been applied such that the mediator may be reoxidized. The oxidized mediator (i.e., ferrocenium) may be then able to accept another electron from the alcohol or lactate conversion reaction to repeat the process. The total charge passing through the sensing electrode is proportional to the amount of alcohol or lactate in the blood that has reacted with the enzyme. Since each ferrocene undergoes one electron oxidation, the oxidation and reduction steps between ferrocene and ferrocenium (e.g., 404, 406, 454, 456), may be performed on two ferrocenes for every analyte molecule in order to transfer to the sensing electrode both electrons that were transferred by NADH. The above reactions are provided merely as examples, and may differ significantly from small variations in the enzyme, electrode structure, or mediator. The number of cycles/molecules used to transfer electrons for each particular mediator is specific to the redox reaction that that mediator undergoes, which may or may not be similar to the ferrocene/ferrocenium reactions.

In various embodiments, the combination of the sensing electrode (e.g., working electrode 110, 214, 318) and a sensing layer film disposed on the surface of the sensing electrode may form a solid state mediated sensor, also referred to herein as a "sensing element." In various embodiments, the sensing layer film may be formed by a polymer, a mediator conjugated (i.e., covalently bonded) to the polymer, and an enzyme immobilized by the polymer with conjugated mediator. In various embodiments, the sensing layer film may be a hydrogel, created by cross-linking of the enzyme and the polymer with conjugated mediator.

In one embodiment, an electron mediator, such as ferrocene (Fc), may be conjugated to the backbone of linear poly(ethyleneimine) to create LPEI-Fc. An NAD-dependent enzyme and l-PEI-Fc may be mixed in various ratios and dispensed over the sensing electrodes in the analysis chamber along with known quantities of crosslinker such as ethylene glycol diglycidyl ether (EGDGE) resulting in a crosslinked LPEI-Fc/enzyme matrix that is smooth and uniform at the air/electrolyte interface.

In transdermal sampling and analysis devices in which the sensing element includes an enzyme that requires a cofactor, the cofactor typically must be present in a high concentration to avoid limiting the reaction and in turn allowing for a proper signal response to be generated. Further, the cofactor must be able to achieve a specific orientation in order for the enzyme-catalyzed reaction to proceed. Therefore, while the enzyme may be immobilized within a hydrogel of the sensing layer film at the surface of the sensing electrode, the cofactor cannot be bound in the same manner That is, to enable effective performance, the cofactor must be readily available at the sensing layer and electrode, and be freeflowing upon wetting of the hydrogel with the interstitial fluid. These requirements have been conventionally been met for cofactor-dependent reactions by adding the cofactor in excess into a bulk solution of interest, into which the electrode with sensing layer may be submerged. However, such process limits application of these reactions to largely non-biological purposes, and is not practical for performing real-time sampling and analysis of biological analytes.

The various embodiment transdermal sampling and analysis devices 100, 200, 300 effectively operate through a coenzyme-dependent enzymatic reactions by the addition of one or more non-bound layer of the cofactor on top of the sensing layer. Specifically, during use of the biosensor, the cofactor may become free-floating in the interstitial fluid that wets the hydrogel. The chamber or channel in which the interstitial fluid contacts the sensing solid state mediated sensor (e.g., in channels 218, 320) may be limited in size to provide a small headspace (e.g., around 10 nL or less). In this manner, a relatively high concentration of the free-floating cofactor may be maintained. Further, the small headspace keeps the free-floating cofactor in close proximity to the sensing layer of the solid state mediated sensor. In various embodiments, the non-bound cofactor layer(s) may be applied using processes that include, but are not limited to, chemical and physical deposition processes.

Figure 5A:
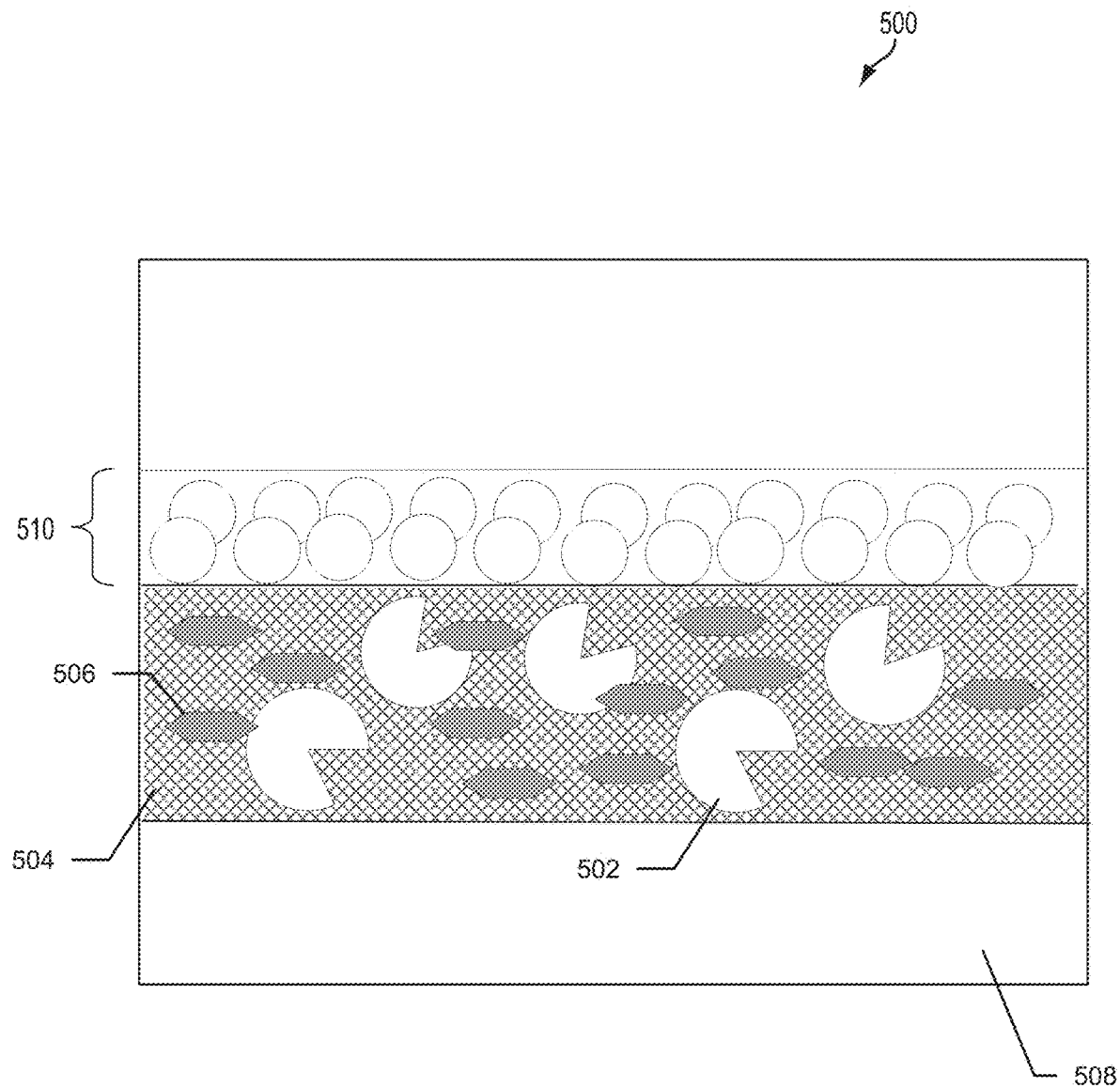
FIGS. 5A and 5B are schematic illustrations of an embodiment sensing element and cofactor layer in a transdermal biosensor.

FIG. 5A illustrates the composition of an example transdermal biosensor 500 that has been prepared with a cofactor according to various embodiments. With reference to FIGS. 1A-5A, an enzyme 502 (e.g., ADH, LDH, etc.) may be immobilized by cross-linking to a redox polymer (e.g., LPEI-Fc), forming an enzymatic redox hydrogel 504. The redox polymer may be formed, for example, by an electron mediator 506 (e.g., ferrocene, ferricyanide, etc.) conjugated or tethered (i.e., connected to a long carbon chain that is conjugated) to a cationic linear polymer (e.g., LPEI). In various embodiments, the enzymatic redox hydrogel 504 may provide a sensing layer on the surface of a sensing electrode 508, which may be a working electrode (e.g., 110, 214, 318) in the transdermal biosensor 500.

In various embodiments, the transdermal biosensor 500 may also include at least one non-bound layer of a cofactor 510 on top of the sensing layer. Specifically, the cofactor 510 may be applied atop the enzymatic redox hydrogel 504 in various embodiments. While the particular cofactor 510 may depend on the analyte of interest and the enzyme utilized in the biosensor, examples include $NAD^+$, FAD, etc.

The mediator 506 of the redox polymer (e.g., Fc-LPEI) may conduct electrons from the cofactor NADH to the surface of the sensing electrode 508.

Figure 5B:
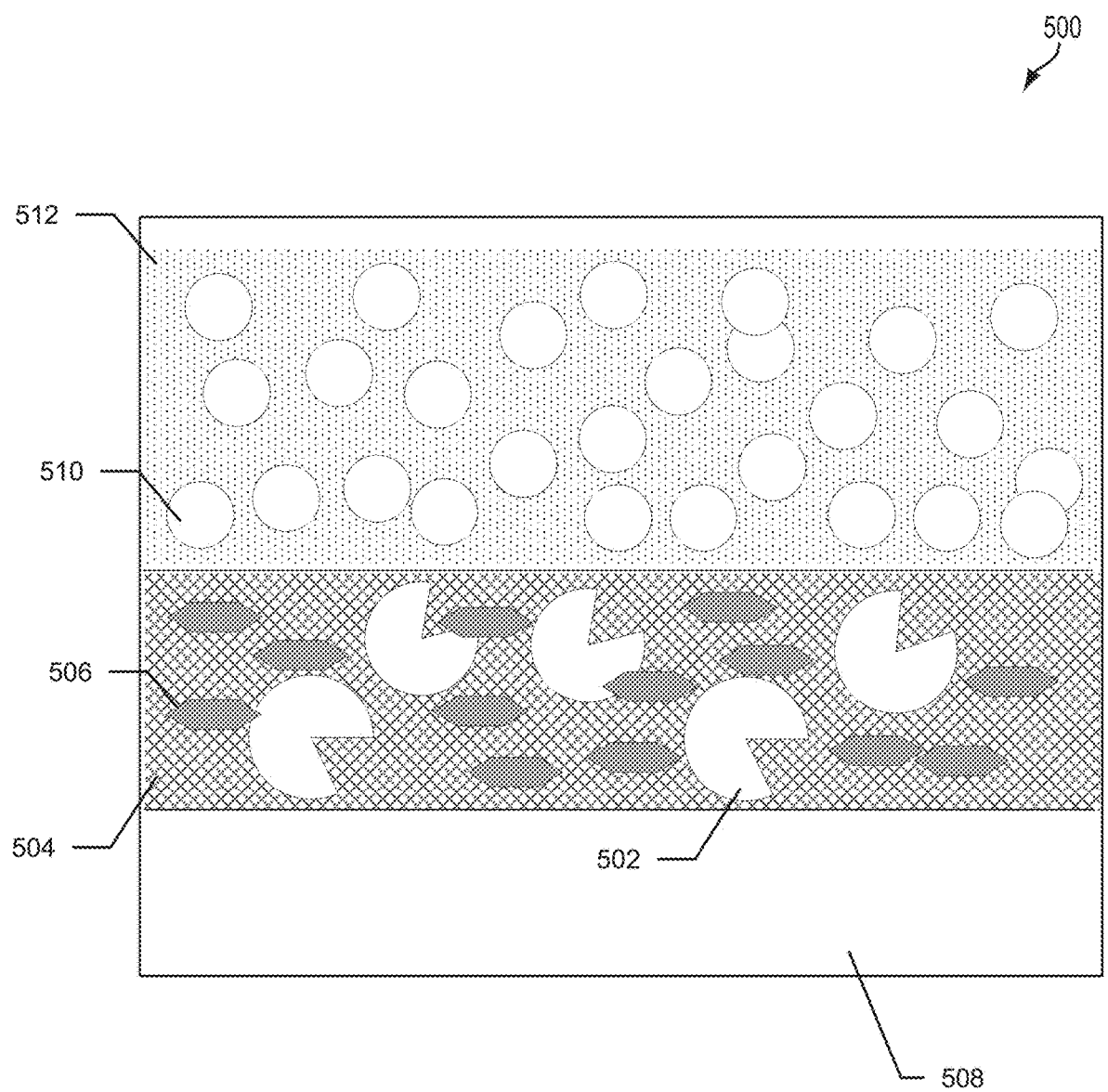

FIG. 5B illustrates the components of the transdermal biosensor 500 during use on a subject. With reference to FIGS. 1A-5B, once the interstitial fluid 512 is introduced, the cofactor 510 that was added in one or more non-bound layer on top of the enzymatic redox hydrogel 504 becomes free-floating. In this manner, the cofactor 510 may be utilized as needed in order for the enzyme-catalyzed reaction to proceed for detection of the analyte of interest.

While discussed with respect to alcohol and lactate detection, the transdermal biosensor 500 may be used in variety of different applications, and may employ any of a number of cofactor-dependent enzyme reactions. Examples of cofactor-dependent enzymes that may be used include digestive enzymes (e.g., amylase, trypsin, lipase, etc.), as well as various metabolic enzymes (e.g., oxidoreductases, hydrolases, lyases, ligases, glucuronidase, transaminases, glycogen synthase, aminoacyl tRNA synthetase, serum glutamic oxaloacetic transaminase, serum glutamic pyruvic transaminase, etc.). Due to the integration of collection and analysis in the same unit, various biological species in the ISF may interfere with the analyte measurements in the transdermal biosensor device of various embodiments. That is, the mediator which, in correct processing, is reduced by the oxidation of the cofactor, may instead be reduced by redox species in ISF that may be strong reducing agents. This transfer of electrons by other molecules may cause the amount of charge measured from the electrodes to no longer be in proportion with the levels of analyte. Therefore, in some embodiments, the sensing element may also include at least one anti-interferent barrier layer applied over the one or more layer of the non-bound cofactor atop the sensing layer. The barrier layer may prevent or limit interfering redox species in the ISF from reaching the sensing element.

In some embodiments, the barrier layer may be charged, and charge type repulsion with charged biological reducing species (i.e., interfering species) prevents interaction between the reducing species and the mediator in the redox hydrogel. The charged barrier layer may be associated with the sensing layer using a variety of forces, such as charge interaction, covalent bonding, van der Waals forces, etc. In various embodiments, the at least one barrier layer may be formed using a variety of materials, including but not limited to alginates, or other anionic naturally occurring polymers. Such materials may be applied to the sensing layer and cofactor layer(s) using processes that include, but are not limited to, chemical and physical deposition processes.

An example biosensor device for detecting ethanol in interstitial fluid may incorporate ADH into a redox hydrogel as part of a sensing layer. To fabricate the sensing layer in the example device, a transport polymer/enzyme solution may be created by combining, in percentages by volume, the following: 65.4% LPEI-Fc dissolved in 0.1M 2-(N-Morpholino)Ethane Sulfonic acid (MES) buffer with 30 mg/mL dilution; 6.5% Ethylene Glycol DiGlycidyl Ether (EGDGE) dissolved in deionized $H_2O$ (15% (w/w) EGDGE) and 85% (w/w) deionized $H_2O$); and 28.1% ADH dissolved in 0.1M MES buffer with 17.63 mg/mL dilution. The combination may be diluted with deionized $H_2O$ in a ratio by volume of 2:1. About 20 layers of the resulting transport polymer/enzyme solution may be sprayed onto the sensing electrode, creating an ADH/LPEI-Fc matrix.

In the example, a cofactor solution may be created by dissolving $NAD^+$ in deionized $H_2O$ with 15 mg/dL dilution. About 30 layers of the cofactor solution may be sprayed following application of the transport polymer/enzyme solution to the sensing electrode. In the example, an interferent blocking solution may be created by dissolving sodium alginate in deionized $H_2O$ with 5 mg/dL dilution. About 10 layers of the interferent blocking solution may be sprayed following application of the cofactor solution.

An example biosensor device for detecting lactate in interstitial fluid may incorporate LDH into a redox hydrogel as part of a sensing layer. To fabricate the sensing layer in the example device, a transport polymer/enzyme solution may be created by combining, in percentages by volume, the following: 65.4% LPEI-Fc dissolved in 0.1M 2-(N-Morpholino)Ethane Sulfonic acid (MES) buffer with 30 mg/mL dilution; 6.5% Ethylene Glycol DiGlycidyl Ether (EGDGE) dissolved in deionized $H_2O$ (15% (w/w) EGDGE) and 85% (w/w) deionized $H_2O$); and 28.1% LDH dissolved in 0.1M MES buffer with 20 mg/mL dilution. The combination may be diluted with deionized $H_2O$ in a ratio by volume of 2:1, and about 20 layers of the resulting transport polymer/enzyme solution sprayed onto the sensing electrode, creating an LDH/LPEI-Fc matrix.

In the example, the sensing element (i.e., LDH/LPEI/Fc matrix and sensing electrode) may be soaked in a solution of 15 mg/mL NAD⁺ and 5 mg/mL alginate dissolved in deionized H$_2$O for thirty minutes. The sensing element may be removed from the solution and rinsed with deionized H$_2$O.

In an embodiment, the various solutions may be applied by dropper, spray, dip, or other coating method appropriate to the sensor system. Thickness of the resulting sensing layer may be, for example, between 0.1 and 10 μm, preferably between 0.2 and 5 μm, and most preferably between 0.5 and 2 μm.

Parameters for creating layers of the sensing element according to the various embodiments, including concentration, temperature, and time, may be adjusted to achieve optimal results.

Figure 6A:
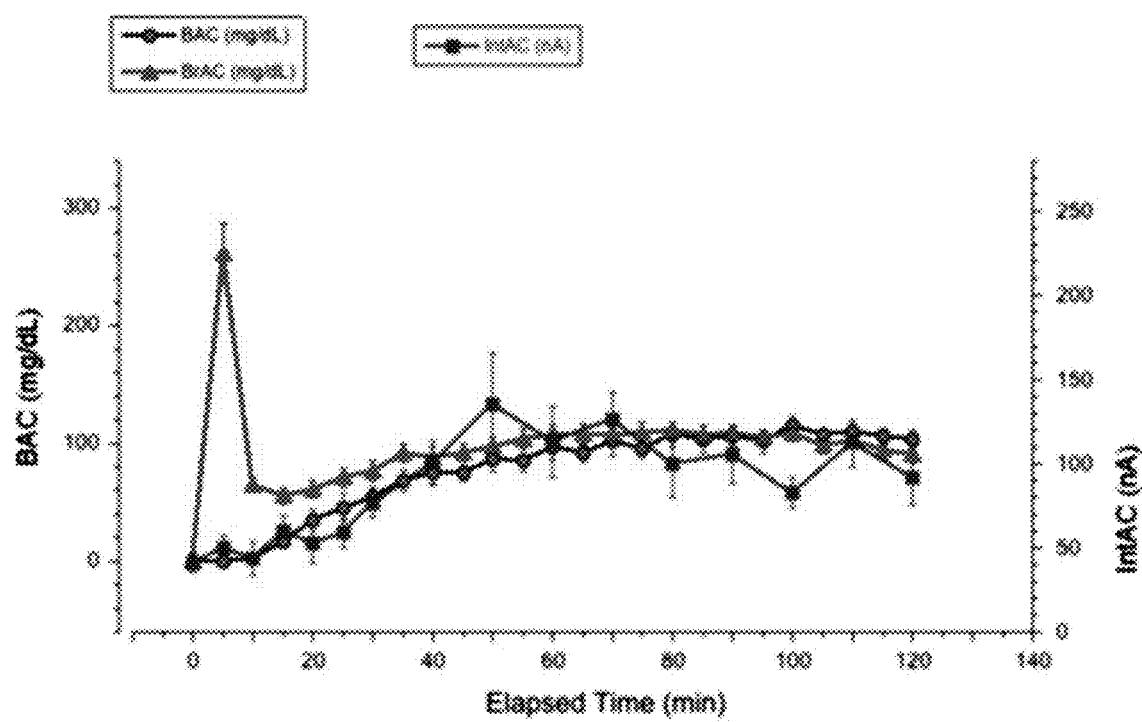
FIG. 6A is a graph showing chronoamperometric current measurement results for alcohol in an embodiment transdermal alcohol biosensor and alcohol concentration results from other technologies.

FIG. 6A shows results from clinical testing of a transdermal biosensor for alcohol prepared using the techniques discussed above, including application of the non-bound cofactor NAD⁺ to the surface of the sensing element. With reference to FIGS. 1A-6A, the plotted data show alcohol detection averaged from 13 subjects who consumed a standard dose of alcohol as a function of time. Specifically, the data was generated over 120 minutes from detection using each of the transdermal alcohol biosensor (i.e., signal generated (nA)), "IntAC," blood alcohol concentration (mg/dL), "BAC," and a breathalyzer device (mg/dL), "BrAC.: Taking blood alcohol concentration as a standard for alcohol detection following consumption, the plotted data show that the transdermal alcohol biosensor provides relatively accurate measurements. Further, the data in FIG. 6B demonstrate that over the first 20 minutes, the transdermal alcohol biosensor showed far greater accuracy compared to the breathalyzer.

Figure 6B:
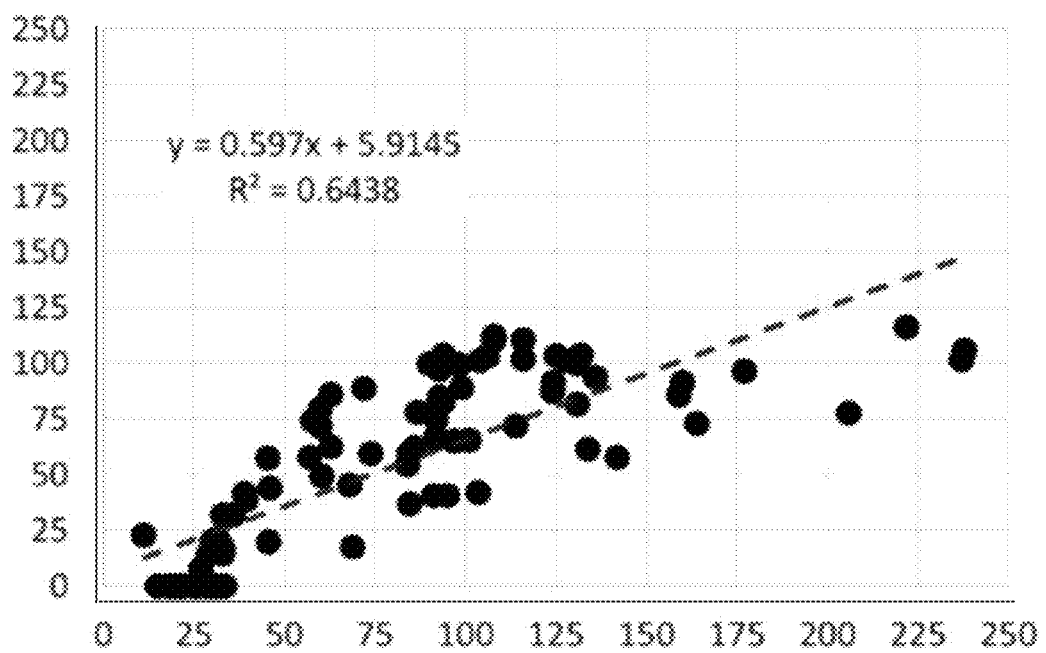
FIG. 6B is a graph comparing chronoamperometric current measurement results for alcohol in an embodiment transdermal alcohol biosensor to blood alcohol concentration results.

FIG. 6B is a regression analysis of the transdermal biosensor and blood alcohol concentration results in FIG. 6A. As shown, there is a strong correlation between results detected using the transdermal alcohol biosensor and results measured using blood alcohol concentration. Consequently, the embodiment transdermal biosensor devices may be deemed to be effective alternatives to competing technologies for analyzing the amount of alcohol consumed by a subject.

Figure 7:
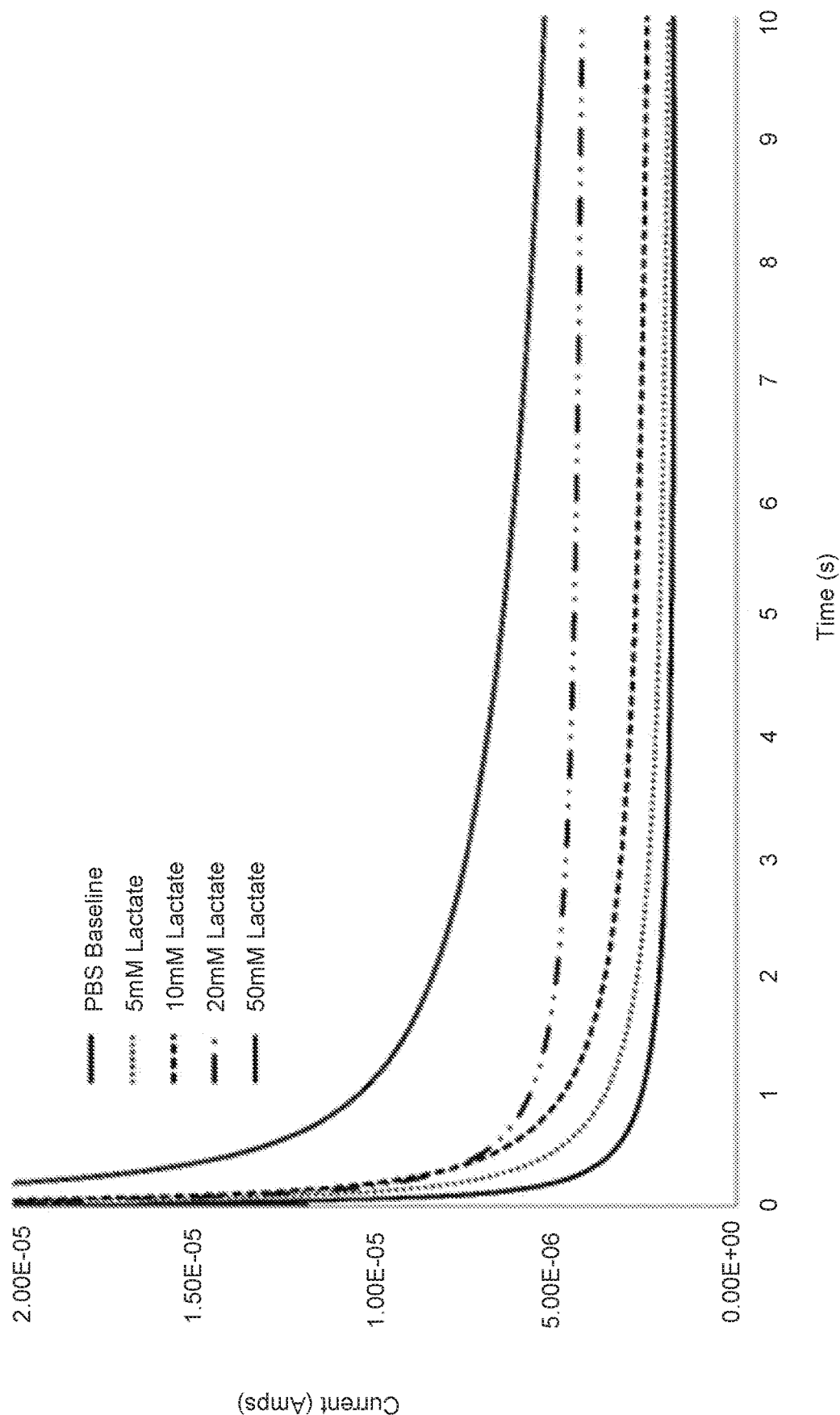
FIG. 7 is a graph showing chronoamperometric current measurement results for lactate in an in vitro sensing element used in an embodiment transdermal lactate biosensor.

FIG. 7 shows results from in vitro testing of a sensing element replicating conditions of a transdermal biosensor for lactate prepared using the techniques discussed above, including application of the non-bound cofactor NAD⁺ to the sensing element. With reference to FIGS. 1A-7, the plotted data show current generated as a function of time for solutions containing known lactate concentrations (0.0, 5, 10, 20, and 50 mM titered solutions in phosphate buffered saline). The results generate an expected progression of the current response proportional to the increasing lactate concentrations over the range of 0 mM to 50 mM. Thus, operations in vitro demonstrate that embodiment transdermal biosensors may be used to provide reliable signaling for measuring lactate concentrations in vivo.

The transdermal sampling and analysis devices/transdermal biosensors of the various embodiments may be manufactured using different methods and materials. Manufacturing methods for an embodiment transdermal sampling and analysis device are disclosed in the related International Application Number PCT/US2006/023194, filed Jun. 14, 2006, entitled "Flexible Apparatus and Method for Monitoring and Delivery," which claims priority to the International Application Number PCT/US2005/044287, entitled "Apparatus and Method for Continuous Real-Time Trace Bimolecular Sampling, Analysis and Deliver," filed on Dec. 9, 2005. The manufacture of an embodiment transdermal sampling and analysis device 100, 200, 300, is also disclosed in the publication entitled "Novel Non-Intrusive Trans-Dermal Remote Wireless Micro-Fluidic Monitoring System Applied to Continuous Glucose and Lactate Assays for Casualty and Combat Readiness Assessment" by John F. Currie, Michael M. Bodo and Frederick J. Pearce, RTO-MP-HFM-109:24-1, Aug. 16, 2004. The entire contents of these related applications and the publication are incorporated by reference herein.

The preceding description of the disclosed aspects is provided to enable any person skilled in the art to make or use the present invention. Various modifications to these aspects will be readily apparent to those skilled in the art, and the generic principles defined herein may be applied to other aspects without departing from the scope of the invention. Thus, the present invention is not intended to be limited to the aspects shown herein but is to be accorded the widest scope consistent with the principles and novel features disclosed herein.

While the invention has been described in detail with respect to specific embodiments thereof, it will be apparent to those skilled in the art that various alterations, modifications and other changes may be made without departing from the scope of the embodiments described herein. It is therefore intended that all such modifications, alterations and other changes be encompassed by the claims. Further, any reference to claim elements in the singular, for example, using the articles "a," "an" or "the" is not to be construed as limiting the element to the singular.

What is claimed is:

1. A transdermal sampling and analysis device comprising:
   a substrate;
   at least one disruptor mounted on the substrate, wherein the at least one disruptor is configured to generate a localized heat capable of altering permeability characteristics of a stratum corneum layer of skin of an organism;
   a reservoir configured to collect and contain a biological fluid sample;
   a sensing element comprising at least two sensing electrodes, wherein a surface of at least one of the sensing electrodes is coated with a sensing layer comprising an enzyme immobilized within a hydrogel; and
   at least one non-bound layer of a cofactor covering the sensing layer, wherein:
      the cofactor is configured to become free-floating upon introduction of the biological fluid sample to the sensing element; and
      the cofactor catalyzes a reaction to determine levels of an analyte in the biological fluid sample.

2. The transdermal sampling and analysis device of claim 1, wherein the biological fluid sample comprises interstitial fluid (ISF), and wherein the enzyme is an oxidoreductase.

3. The transdermal sampling and analysis device of claim 2, wherein the cofactor comprises oxidized nicotinamide adenine dinucleotide (NAD⁺).

4. The transdermal sampling and analysis device of claim 2, wherein the oxidoreductase is selected from alcohol dehydrogenases or lactate dehydrogenases.

5. The transdermal sampling and analysis device of claim 1, wherein the hydrogel of the sensing layer comprises a plurality of cross-linked hydrophilic polymer chains.

6. The transdermal sampling and analysis device of claim 5, wherein the cross-linked hydrophilic polymer chains comprise a linear poly(ethylenimine) (LPEI) coupled to an electron mediator.

7. The transdermal sampling and analysis device of claim 6, wherein the electron mediator is selected from the group consisting of a ferrocene, osmium bipyridine complexes, ruthenium phthalocyanine complexes, a quinone, a tetrathialfulvalene (TTF), a tetracyanoquinodimethane (TCNQ), or a thionine.

8. The transdermal sampling and analysis device of claim 1, wherein the at least one non-bound layer of the cofactor is covered with at least one barrier layer comprising alginate.

9. The transdermal sampling and analysis device of claim 1, wherein the at least one non-bound layer of the cofactor further comprises alginate.

10. A method of determining levels of an analyte in a biological fluid sample, the method comprising:
   providing at least one disruptor mounted on a substrate, wherein the at least one disruptor is configured to generate a localized heat capable of altering permeability characteristics of a stratum corneum layer of skin of an organism;
   providing a reservoir configured to collect and contain the biological fluid sample;
   providing a sensing element, comprising:
      at least two sensing electrodes, wherein a surface of at least one of the sensing electrodes is coated with a sensing layer comprising an enzyme immobilized within a hydrogel; and
   applying at least one non-bound layer of a cofactor atop the sensing layer, wherein the cofactor is configured to become free-floating upon introduction of the biological fluid sample to the sensing element and catalyzes a reaction to determine levels of an analyte in the biological fluid sample; and
   providing the biological fluid sample to the sensing element and the at least one non-bound layer of the cofactor.

11. The method of claim 10, wherein the sensing element and the at least one non-bound layer of the cofactor are housed within a chamber, wherein the chamber is configured to accommodate up to 10 nL of the biological fluid sample.

12. The method of claim 10, wherein the biological fluid sample comprises interstitial fluid (ISF), and wherein the enzyme is an oxidoreductase.

13. The method of claim 12, wherein the cofactor comprises oxidized nicotinamide adenine dinucleotide (NAD+).

14. The method of claim 12, wherein the oxidoreductase is selected from alcohol dehydrogenases or lactate dehydrogenases.

15. The method of claim 10, wherein the hydrogel comprises a plurality of cross-linked hydrophilic polymer chains.

16. The method of claim 15, wherein the cross-linked hydrophilic polymer chains comprise a linear poly(ethylenimine) (LPEI) coupled to an electron mediator.

17. The method of claim 16, wherein the electron mediator is selected from the group consisting of a ferrocene, osmium bipyridine complexes, ruthenium phthalocyanine complexes, a quinone, a tetrathialfulvalene (TTF), a tetracyanoquinodimethane (TCNQ), and a thionine.

18. The method of claim 10, further comprising applying one or more layers of alginate atop the at least one non-bound layer of the cofactor.

19. The method of claim 10, wherein the at least one non-bound layer of the cofactor further includes alginate.

* * * * *